US008468032B2

(12) United States Patent
Van Hoe (10) Patent No.: US 8,468,032 B2
(45) Date of Patent: Jun. 18, 2013

(54) METHOD FOR TELERADIOLOGICAL ANALYSIS (76) Inventor: Lieven Van Hoe, Aalst (BE)

(*) Notice: Subject to any disclaimer, the term of this patent is extended or adjusted under 35 U.S.C. 154(b) by 645 days.

(21) Appl. No.: 12/373,031

(22) PCT Filed: Jul. 13, 2006

(86) PCT No.: PCT/EP2006/006832
§ 371 (c)(1),
(2), (4) Date: Feb. 4, 2009

(87) PCT Pub. No.: WO2008/006389
PCT Pub. Date: Jan. 17, 2008

(65) Prior Publication Data
US 2010/0138230 A1   Jun. 3, 2010

(51) Int. Cl.
*G06Q 50/00*   (2006.01)
(52) U.S. Cl.
USPC ............................................................ 705/2
(58) Field of Classification Search
USPC ....................................................... 705/2–3
See application file for complete search history.

(56) References Cited

U.S. PATENT DOCUMENTS

| | | | |
|---|---|---|---|
| 5,655,084 A * | 8/1997 | Pinsky et al. ...................... 705/3 |
| 7,765,109 B2 * | 7/2010 | Gutman et al. .................... 705/2 |
| 7,813,942 B2 * | 10/2010 | Rose .................................. 705/3 |
| 2004/0061889 A1 * | 4/2004 | Wood et al. .................. 358/1.15 |
| 2004/0064037 A1 * | 4/2004 | Smith ............................. 600/420 |
| 2005/0114181 A1 * | 5/2005 | Gottlieb ............................. 705/2 |
| 2005/0114380 A1 * | 5/2005 | Eldar et al. ..................... 707/102 |
| 2006/0274145 A1 * | 12/2006 | Reiner ............................. 348/62 |
| 2007/0179811 A1 * | 8/2007 | Reiner .............................. 705/2 |

* cited by examiner

*Primary Examiner* — Luke Gilligan
*Assistant Examiner* — Robert Sorey
(74) *Attorney, Agent, or Firm* — Knobbe Martens Olson & Bear LLP (57) ABSTRACT

A system and method is described for building a community of clients and radiologists. The method and system bring clients i.e. persons or organisations requiring the analysis of radiographic images, together with radiologists i.e. persons or organisations qualified to undertake analyses of radiographic images. The clients and radiologists register their respective requirements and services with the system, the system matching a suitable client to a suitable radiologist. The method and system use an algorithm to match client and radiologist(s) most effectively. A open feedback facility in which the client indicates his satisfaction with the radiologist (e.g. quality of report, timeliness, cost), and in which the radiologist also indicates his satisfaction with the client (e.g. image quality, quality of associated data, timely payment) is implemented so the quality of service and client of a teleradiology community evolves and high standards are achieved.

19 Claims, 5 Drawing Sheets

METHOD FOR TELERADIOLOGICAL ANALYSIS

CROSS-REFERENCE TO RELATED APPLICATIONS

This application is the U.S. National Phase under 35 U.S.C. §371 of International Application PCT/EP2006/006832, filed Jul. 13, 2006.

BACKGROUND TO THE INVENTION

Teleradiology is a means of electronically transmitting radiographic patient images and consultative text from one location to another. It is commonly employed when the equipment and personnel for recording the radiographic image are located in one location, and the expert in radiological image analysis, the radiologist, is situated in a remote location. Different connection configurations exist in the art, which are elaborated below.

In a point-to-point connection system, the recorded images are transmitted from a sending station together with the relevant associated data, to a remote receiving station. A radiologist views the images and associated data at the receiving station and generates a report. The report is sent back to the required location, be it to the originator of the request or to the referring clinician. The referring clinician can be located proximal to the sending station e.g. in the same hospital where the image was taken, or elsewhere. The point to point access relies the sending party finding a reliable receiving party which can provide a quality analysis within a requested timeframe for a reasonable cost. The receiving party must be able to cope with urgent or a large quantity of requests, and yet must avoid running at overcapacity during times of routine workloads.

Another model is where several sending stations each with a different location, for example, in different hospitals or imaging centers, are linked to a single receiving station which is a teleradiology group. Teleradiology group employs radiologists to analyse images and prepare reports. The completed reports are sent back to the required location, be it to the originator of the request or to the referring clinician. The teleradiology group provides the analysis service by recruiting radiologists according to their training and expertise. A higher premium is paid for such service because the costs of administering the teleradiology group (e.g. infrastructure, radiologist recruitment, image distribution, quality control, promotion) in addition to the radiologist fees must be met.

A further defined model to the teleradiology group is the teleradiology hub, where several sending stations each with a different location, for example, in different hospitals or imaging centers, are linked to a single receiving station which is a teleradiology hub. The Teleradiology hub may employ a local team of radiologists as in the teleradiology model, but may also distribute the images remotely for analysis to radiologists who may be experts or specialists in particularly defined field. The specialisation can be so narrow and infrequently required that it is not available in the vicinity of the hub. The costs to the client of a service provided by a Teleradiology hub are comparatively high, and the hub must still locate reliable and reasonably-priced specialist radiologists, within a specified timeframe.

The problem posed in the art by teleradiology is how to achieve flexibility, quality and cost effectiveness. The separate methods of the art do not all provide a system that can manage high and low demand, urgent and routine requests, specialist analyses, reliable and quality radiologists, all for a reasonable cost. The aim of the present invention is a method and system for radiological analyses that overcomes the problems of the prior art.

SUMMARY OF SOME EMBODIMENTS OF THE INVENTION

One embodiment of the present invention is a method for assisting in the analysis of a client's radiographic imaging study by a remote radiologist, comprising the steps:
a) receiving (5) registration details of one or more radiologists (1), including an indication of their characteristics (4),
b) receiving (6) registration details of one or more clients (3), including an indication of their characteristics (6),
c) receiving (9) an imaging study (10) and associated data sent by a registered client (3),
d) selecting (8) one or more registered radiologists (1) to analyse an imaging study (10) by matching the radiologists' characteristics (4) with the characteristics of the client (7) and associated data of the imaging study (10) of step c),
e) making available (12) to said selected registered radiologists, a worklist (11) of imaging studies sent by clients,
f) receiving (22) a report (21') of said analysed imaging study prepared by a registered radiologist (1) of step e),
g) making available (31) the report (21''') of step f) to the registered client (3) of step c),
h) receiving (27) a feedback score (29) from the registered client 1 regarding the quality of the registered radiologist's report (21'''),
i) receiving (25) a feedback score (28) from the registered radiologist (3) regarding collaboration with the client (1),
j) calculating a rating profile (26) of the registered radiologist (2) and client (3) based on received feedback scores (28, 29).

Another embodiment of the present invention is a method as described above, wherein the worklist of step e) is ranked according to urgency.

Another embodiment of the present invention is a method as described above, wherein the most urgent imaging study is removed from the worklist of step e) after receiving an indication that one of the selected radiologists (1) has opened said imaging study.

Another embodiment of the present invention is a method as described above, wherein the most urgent imaging study is removed from the worklist of step e) after the report of step f) has been received.

Another embodiment of the present invention is a method as described above, further comprising a step after step e) of: receiving an indication from a selected radiologist (1) of an interest in analysing the most urgent imaging study or a non-interest in analysing the most urgent imaging study.

Another embodiment of the present invention is a method as described above, wherein the most urgent imaging study is removed from the worklist of step e) after receiving said indication.

Another embodiment of the present invention is a method as described above comprising the step of making available the rating profile (26) of said radiologist (1) and client (3) to all registered radiologists and clients.

Another embodiment of the present invention is a method as described above wherein the characteristics of the client (3) include one or more of:
 preferred geographical location of the radiologist (1),
 maximum fee and/or fee range, and
 any other characteristic.

Another embodiment of the present invention is a method as described above, wherein the characteristics of the radiologists (1) include one or more of:
indication of which countries, regions, countries, localities and/or hospitals he wishes to work,
indication of the type(s) of imaging study or studies he wants to analyse,
indication of whether he wants to act as a primary reader, as secondary reader, or both,
indication of the desired fee for carrying out an analysis of a particular image study,
the wish to display a curriculum vitae
indication of availability,
indication of availability for STAT readings,
an indication of willingness to work together with one or more other registered radiologists to form a reading group,
any other characteristic.

Another embodiment of the present invention is a method as described above, wherein said reading group is permitted when availability for STAT readings is indicated.

Another embodiment of the present invention is a method as described above, where the type of imaging study is selected according to one or more of the following criteria:
type of imaging instrument,
body part, and
patient characteristic.

Another embodiment of the present invention is a method as described above, wherein the ranking is determined by
the time of arrival of images at the central database and/or
a requested turnaround time by the client (3).

Another embodiment of the present invention is a method as described above, wherein the worklist of step e) is filtered to exclude clients refused by said radiologist (1).

Another embodiment of the present invention is a method as described above, wherein the worklist of step e) is filtered to exclude clients which have refused said radiologist (1).

Another embodiment of the present invention is a method as described above where a radiologist receives an alert when his worklist has been updated.

Another embodiment of the present invention is a method as described above, when said alert is by telephone, SMS messaging or email.

Another embodiment of the present invention is a computer program held on a computer readable medium for assisting in the analysis of clients' radiographic image study by remote radiologists, which computer program is capable of performing a method as described above.

Another embodiment of the present invention is a system for assisting in the analysis of clients' radiographic image study by remote radiologists, which system is capable of performing a method as described above.

Another embodiment of the present invention is a system as described above, comprising a processing means (39) whereby,
a) said means (39) is configured to make available over the Internet (34) a web page for the entry on a remote computer (38) of registration details of one or more radiologists, including an indication of their characteristics,
b) said means (39) is configured to make available over the Internet (34) a web page for the entry viewing on a remote computer (37) of registration details of one or more clients, including an indication of their characteristics,
c) said means (39) is configured to receive electronically an imaging study and associated data sent by a registered client from a remote computer (37),
d) said means 39 is configured to select a registered radiologist to analyse an imaging study by matching the radiologists' characteristics with the characteristics of the client and associated data of the imaging study of c),
e) said means (39) is configured to available over the Internet (34) to the registered radiologist or send electronically thereto, a list of imaging studies sent by clients,
f) said means (39) is configured to receive electronically a report of said analysed imaging study prepared by a registered radiologist of step d),
g) said means (39) is configured to make available over the Internet (34) to registered client of step c) or send electronically thereto, the report of step f),
h) said means (39) is configured to make available over the Internet (34) a web page for receiving a feedback score from the registered client regarding the quality of the registered radiologist's report,
i) said means (39) is configured to make available over the Internet (34) a web page for receiving a feedback score from the registered radiologist regarding collaboration with the client,
j) said means (39) is configured to calculate a rating profile of the registered radiologist and client based on received feedback scores.

DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The articles "a" and "an" are used herein to refer to one or to more than one, i.e. to at least one of the grammatical object of the article. By way of example, "a radiologist" means one radiologist or more than one radiologist.

Throughout this application, the term "about" is used to indicate that a value includes the standard deviation of error for the device or method being employed to determine the value.

The recitation of numerical ranges by endpoints includes all integer numbers and, where appropriate, fractions subsumed within that range (e.g. 1 to 5 can include 1, 2, 3, 4 when referring to, for example, a number of clients, and can also include 1.5, 2, 2.75 and 3.80, when referring to, for example, a rating).

The present invention provides a system and method for building a community of clients and radiologists.

The method and system bring clients i.e. persons or organisations requiring the analysis of radiographic images, together with radiologists i.e. persons or organisations qualified to undertake analyses of radiographic images. The method and system allow clients to choose from a range of radiologists according to, for example, geographical location, training, qualification, specialisation, availability, fee and reputation. It also permits free-lance radiologists to locate suitable clients, and to perform analyses at a time and location to suit their other commitments.

The method and system are based on a client and radiologist registering their respective requirements and services with the system, and the system matching a suitable client to a suitable radiologist. The client provides some information about the study needing analysis, for example, the recording instrument (e.g. computed tomography scanner), body part (e.g. brain), patient characteristics (e.g. adolescent male), while the radiologist provides information about his qualifications, specialisations and preferences. The method and system use an algorithm to match client and radiologist(s) most effectively.

Because the method and system use a simple registration procedure, ideally implemented over the Internet, a large community of clients and radiologists is quickly built. A pool of radiologists, therefore, becomes available to serve clients, whatever the required capacity, specialisation or deadline. Being semi-automated, the invention has low overheads and can thus provide a service that is cost-effective to the client, and allows the radiologist to retain most of his fee.

Furthermore, a feedback facility in which the client indicates his satisfaction with the radiologist (e.g. quality of report, timeliness, cost), and in which the radiologist also indicates his satisfaction with the client (e.g. image quality, quality of associated data, timely payment) is implemented in the method and system. The feedback is used to produce a rating that can be available to anyone registered in the system. It quickly becomes in the interests of both the client and the radiologist to clearly define their requirements and services, and to deliver accordingly. Therefore, the quality of service and client of a teleradiology community evolves, the openness of feedback providing the necessary motivation for consistently high standards.

Figure 1:
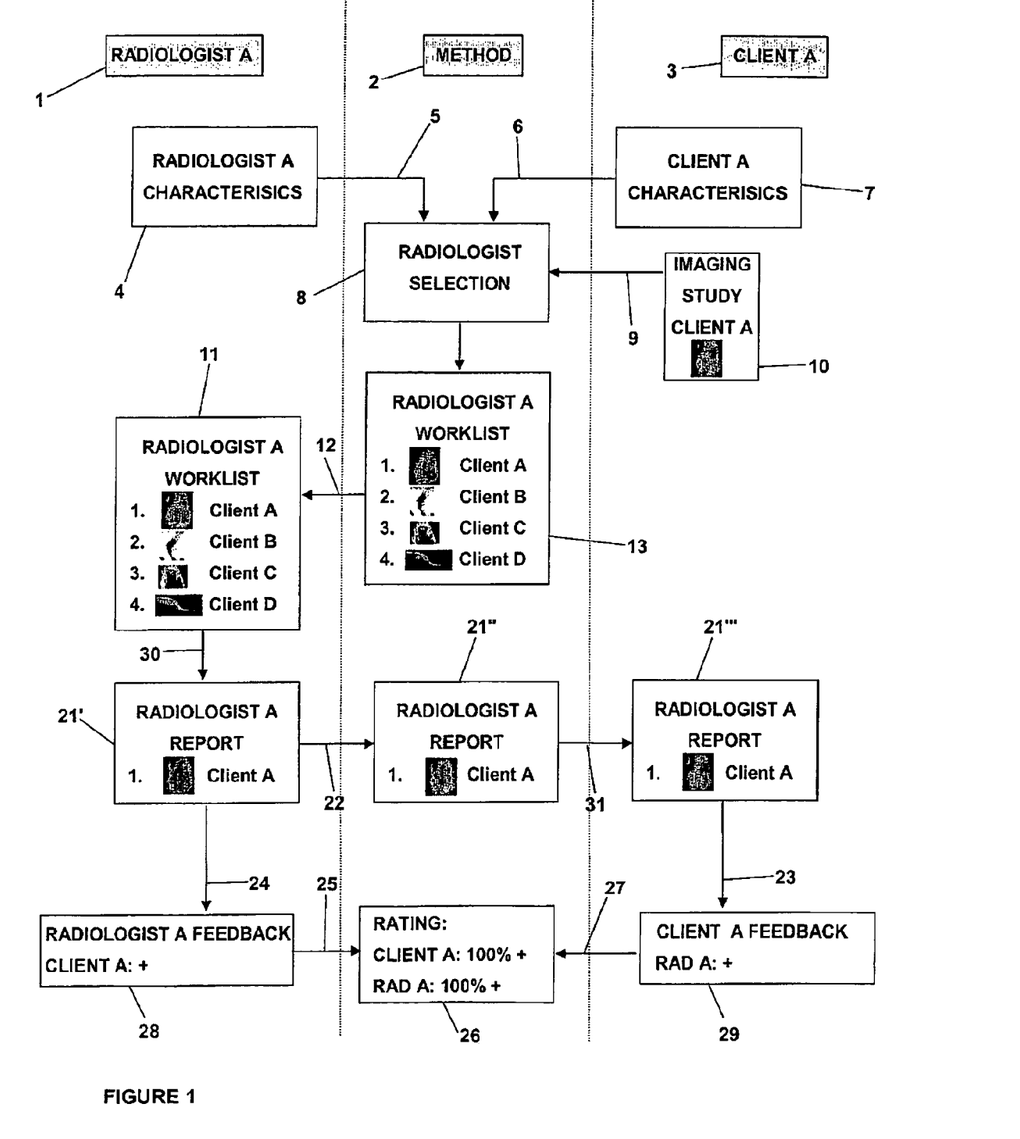
FIG. 1. Overview of a method of the invention.

The description below makes reference to the figures which exemplify particular embodiments of the invention; they are not at all intended to be limiting. The skilled person may adapt the method and substituent steps and features according to the common practices of the person skilled in the art. With reference to FIG. 1, the present invention relates to a method for assisting in the analysis of a client's radiographic imaging study by a remote radiologist, comprising the steps:
a) receiving 5 registration details of one or more radiologists 1, including an indication of their characteristics 4,
b) receiving 6 registration details of one or more clients 3, including an indication of their characteristics 6,
c) receiving 9 an imaging study 10 and associated data sent by a registered client 3,
d) selecting 8 one or more registered radiologist(s) 1 to analyse an imaging study 10 by matching the radiologists' characteristics 4 with the characteristics of the client 7 and associated data of the imaging study 10 of step c),
e) making available 12 to said selected registered radiologists, a list 11 of imaging studies sent by clients,
f) receiving 22 a report 21' of said analysed imaging study prepared by a registered radiologist 1 of step d),
g) making available 31 the report 21''' of step f) to the registered client 3 of step c),
h) receiving 27 a feedback score 29 from the registered client 1 regarding the quality of the registered radiologist's report 21''',
i) receiving 25 a feedback score 28 from the registered radiologist 3 regarding collaboration with the client 1, and
j) calculating a rating profile 26 of the registered radiologist 1 and client 3 based on received feedback scores 28, 29.

The client is the individual or organisation requiring the analysis of radiographic images. It may be a hospital, a hospital department, a referring clinician etc. The client is preferably the legal entity (e.g. person, organisation) that agrees with conditions for registration. The registration may request the client to confirm his legally binding agreement with or confirmation of one or more of the following:
  address and contact details (e.g. email address, postal address and/or telephone number).
  agreement to payment of fees,
  agreement to the conditions of registration.

Registration can performed be online via the Internet, by email, by SMS, by the completion of a signed contract, or any suitable route.

The registration for a client 3 may also include an indication of their characteristics 7, which can include any of:
  preferred geographical location for the radiologist,
  maximum fee and/or fee range, and
  any other characteristic.

After completion of registration, and an optionally indication of their characteristics, the client can provide a radiographic image for analysis, along with data related to the image and optionally preferences for the radiologist.

The radiologist 1 is normally the person qualified to undertake analyses of radiographic images. The radiologist 1 is preferably the legal entity (e.g. person) that agrees with conditions for registration. The registration may request the radiologist to confirm his legally binding agreement or confirmation of one or more of the following:
  contact details of the radiologist, e.g. email address, postal address and/or telephone number,
  he is qualified as medical doctor and/or radiologist in the country where he lives and/or works,
  he has the relevant medicolegal insurance,
  he submits to the jurisdiction of the country where the radiographic image has been taken has been performed,
  he will adhere to the highest professional standards when practicing as teleradiologist,
  he agrees to the conditions of registration.

Registration can performed be online via the Internet, by email, by SMS messaging, by the completion of a signed contract, or by any other suitable route. The radiologist may also be required to provide documentary evidence (e.g. a certificate or license that he is qualified to practice and has medicolegal insurance).

Another aspect of the registration for a radiologist 1 may be the further indication of their characteristics 4, which include any of their fees, areas of expertise, preferred geographical location for working, and availability. In detail, radiologist may indicate during or after registration one of more of the following characteristics:
  indication of which countries, regions, countries, localities and/or hospitals he wishes to work,
  indication of the type(s) of imaging study or studies he wants to analyse. According to one aspect of the invention, these can be chosen from selection menus, such as pull down menus or tick boxes. The choices available to the radiologist may include, but are not limited to:
    type of imaging instrument (e.g. computed tomography, magnetic resonance imaging, X ray, . . . )
    body part (e.g. brain, head and neck, lungs, heart, upper abdomen, pelvis, musculoskeletal, breast, . . . )
    patient characteristic (e.g. age, gender)

indication of whether he wants to act as a primary reader (i.e. the radiologist who is given the image to make the substantive analysis), as secondary reader, or both, indication of the desired fee for carrying out an analysis of a particular image study, the wish to display a curriculum vitae, which CV can be typed or uploaded to the system, indication of availability, indication of availability for STAT (i.e. urgent) readings. This might include an indication of the particular image study (see viii), the requested fee, and availability for urgent work (e.g. available Monday-Friday between 9 am and 6 pm GMT)

indication of willingness to work together with one or more other registered radiologists to form a reading group. Said reading group may be permitted when availability for STAT readings is indicated The reading group being a collection of registered radiologists can assume a new single name. The reading group would be able to cover holiday periods for example. The radiologist can specify names of other group member(s), any other characteristic.

The above criteria can be subsequently updated by the radiologist.

The registered client 3 having an imaging study 10 of a subject may proceed to send 9 the study for analysis. The images may be sent electronically in any suitable format (e.g. DICOM, JPEG, pdf, TIFF, PICT). It can be uploaded using a web page, sent by email or any other suitable way of sending electronic information. Data associated with the study may also be sent as part of the study. Such data may include one or more of the following:

relevant clinical information, specific requests to the radiologist, type of imaging instrument (e.g. computed tomography, magnetic resonance imaging, X ray, . . . ), body part (e.g. brain, head and neck, lungs, heart, upper abdomen, pelvis, musculoskeletal, breast, . . . ), patient characteristic (e.g. age, gender), address to which the report should be sent (e.g. email address, URL, FTP site), date or time limit for completing and submitting the report, maximum fee and/or free range.

The more information and detail provided by the client, the better a radiologist can be matched, and also the better the quality of the report.

Having received an imaging study and associated data, one or more registered radiologists 1 is chosen by the invention to analyse the study, by matching 8 the radiologists characteristics 4 with those of the client 3 and with the data associated with the study 10. A list of work (worklist) 13 is thus created and made available 12 for the radiologist 1, for viewing 11 at his remote location, which lists contains studies the radiologist is suited to analyse. The worklist can be made available over the Internet. It can also be provided to the radiologist by other means such as email or SMS messaging. An alert may be provided to the radiologist 1 by for example, telephonically, by email, SMS messaging or RSS when the worklist has been updated, for example by the addition of new imaging studies, or removal of completed or withdrawn studies.

Where several radiologist appear to have the right criteria, the same study may appear on multiple worklists; in such case, the first radiologist to indicate a committing interest in analysing the study is chosen.

Figure 2:
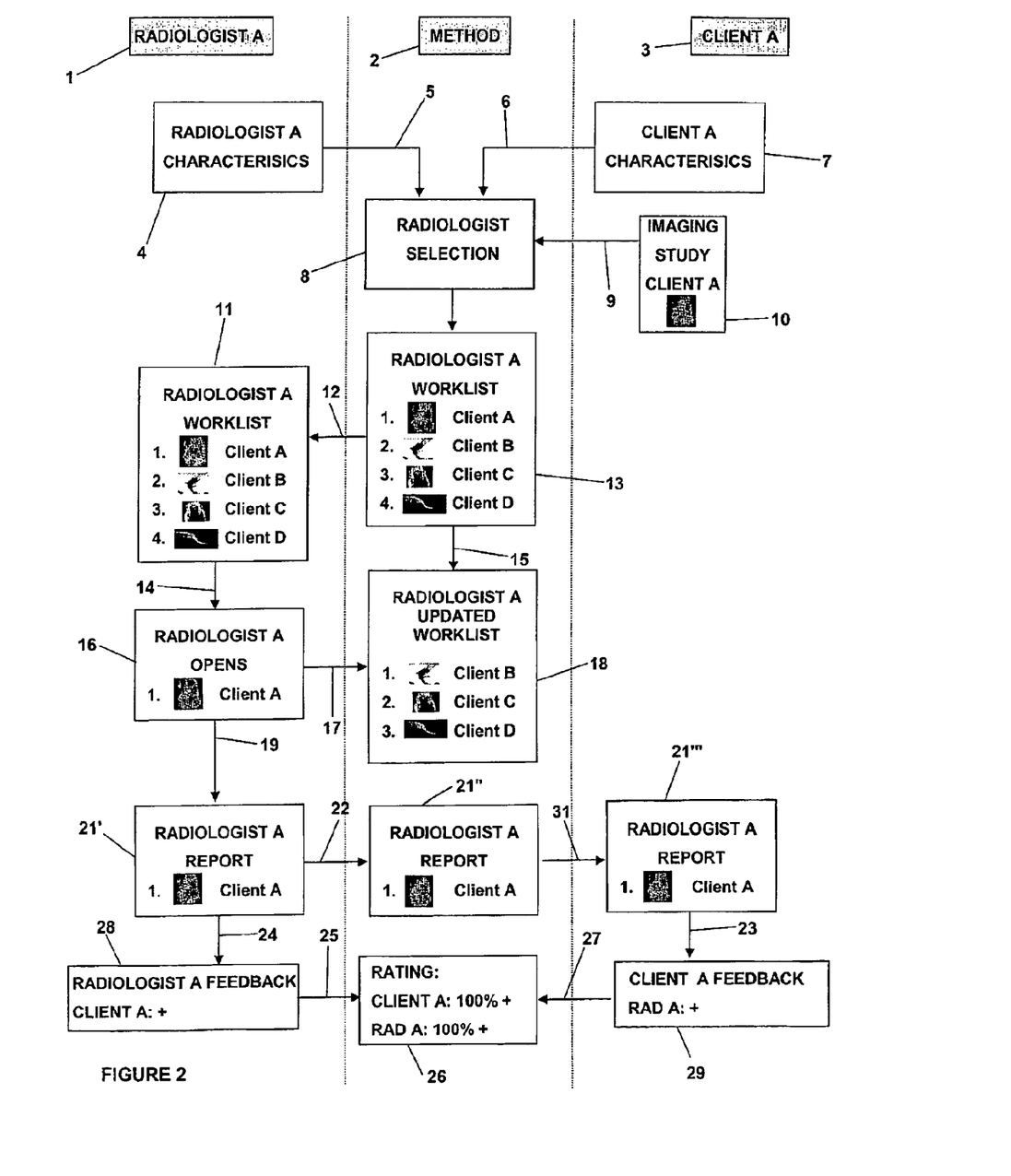
FIG. 2. Overview of a method of the invention, with a detail of worklist updating after the radiologist opens a study.

Imaging studies in a worklist 11, 13 can be accessed by the radiologist 1, one by one in the order they are ranked. This is exemplified in FIGS. 1 and 2, where the worklist 11 viewed by the radiologist 1 contains four items, ranked in order of urgency from 1 to 4 for clients A to D respectively. For each study, the remaining time before the report deadline may be indicated. Preferably, the study displayed at the top of the list should be read first by the radiologist 1. The rankings of studies in the worklist 11 may be determined by any relevant criteria including, for example:

the time of arrival of images at the central database and/or requested turnaround time by client.

The ranking is preferably determined by the method in order of urgency, and not by the radiologist.

The radiologist may not be permitted to make a report on any study other than the highest ranking study. As the invention matches an imaging study to the requirements of the radiologist, the highest ranking study should be within the availability, skill, fee range and time-availability of the radiologist.

According to one aspect of the invention, the radiologist is committed to make a report of the imaging study by opening (e.g. downloading, viewing on screen) the imaging study.

In one embodiment of the invention, once an indication is received that the radiologist (1) has opened the most urgent study, the radiologists' worklists are updated. An example is given in FIG. 2 where the radiologist 1 opens 16 the highest ranking imaging study, which is the study was submitted by client A. The worklist is subsequently updated 15, so that the next highest ranking request in this case, that of client B, is indicated in a new worklist 18. Where several radiologist appear to have the right criteria, the same study may appear on multiple worklists; in such case, the first radiologist to open the study is chosen.

According to another aspect of the invention, the highest ranking imaging study is not removed from a radiologists worklist until a report thereon has been received by the system. This embodiment is exemplified in FIG. 3, where the radiologist submits a report 21' regarding the highest ranking request. The previous worklist 13 is only updated 15 after the report 21" has been received 17 by the system or method. The updated worklist 18 is available 40 for viewing by the radiologist 1. Where several radiologist appear to have the right criteria, the same study may appear on multiple worklists; in such case, the study, once opened, may be removed from all radiologists' worklists except that of the first radiologist to open the study.

Figure 3:
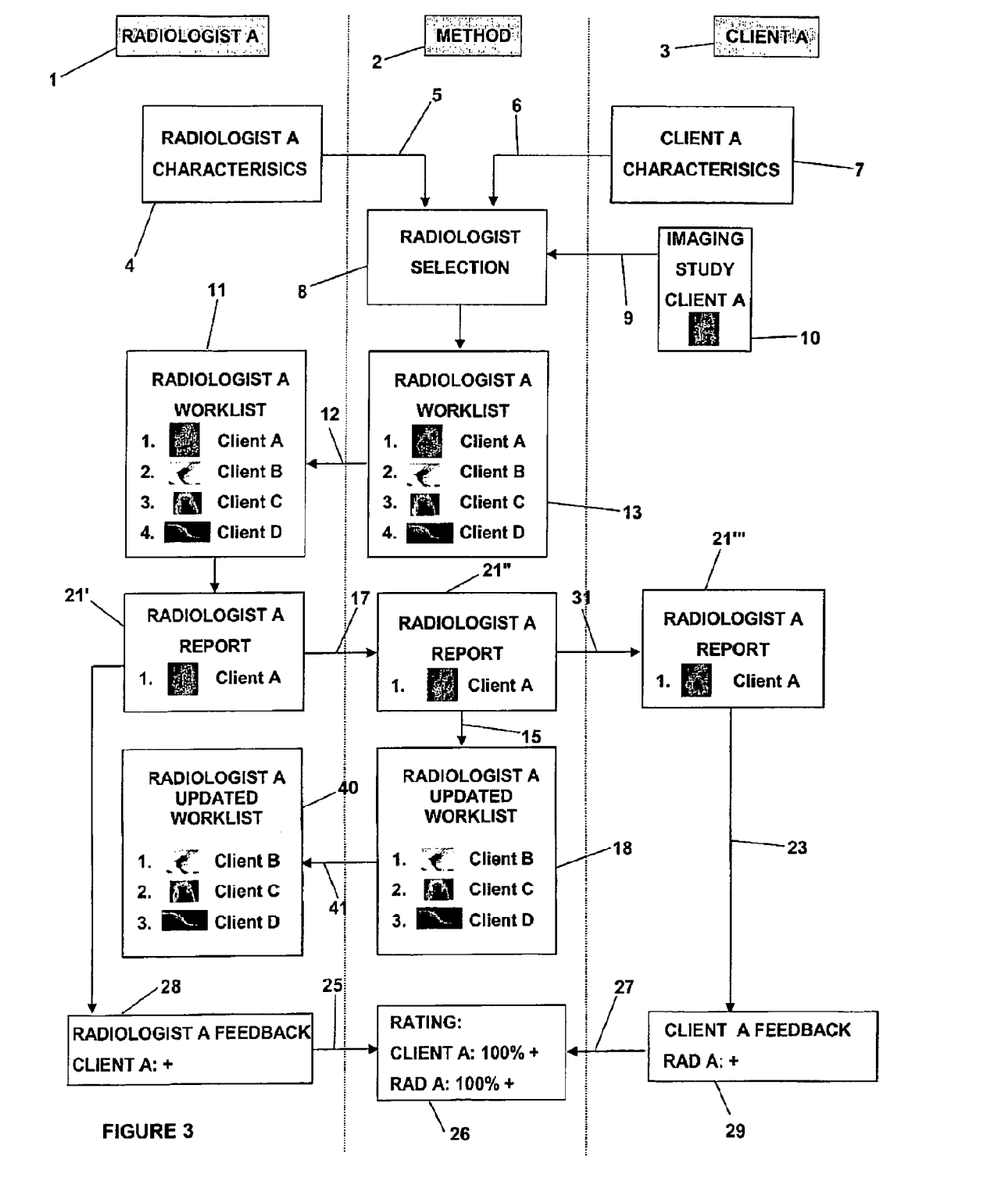
FIG. 3. Overview of a method of the invention, with a detail of worklist updating after the radiologist submits a report.
Figure 4:
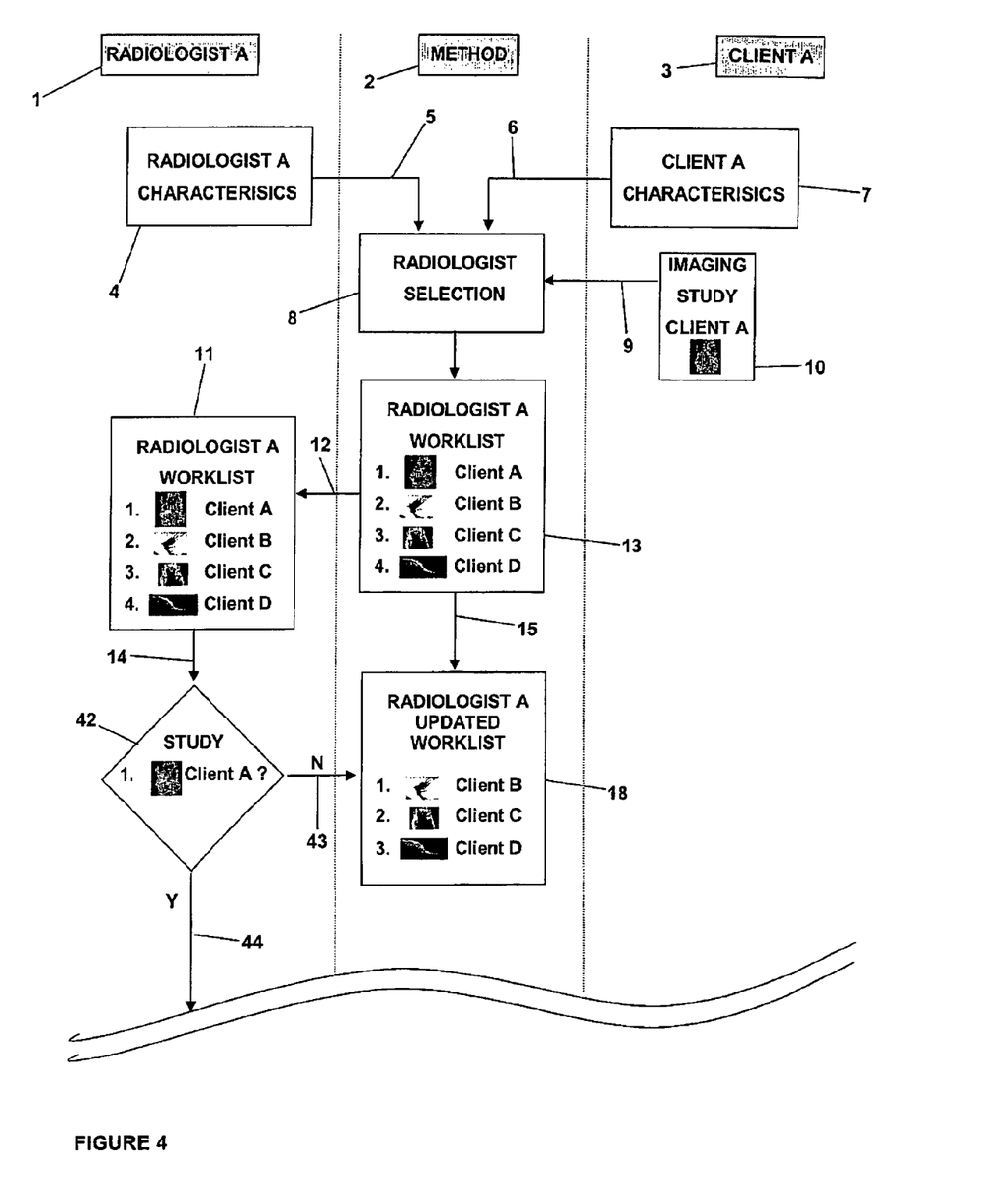
FIG. 4. Overview of a method of the invention, with a detail of worklist updating after the radiologist indicates his commitment or not to prepare a report on an imaging study.

According to another aspect of the invention, the radiologist 1 being presented with his worklist 11 can agree, or not, to make a report of the first item on the list 42 (FIG. 4). The radiologist can indicate his commitment in analysing the first study by, for example, indicating 'Yes' 44. By indicating 'Yes', the radiologist may be committed to prepare a report, and worklists can be updated immediately or after the final report is submitted as described above, and depicted in FIGS. 2 and 3.

Alternatively, he may indicate, for example, 'No' 43 to have the report removed from his worklist, in which case the worklist is updated 18. Thus, another embodiment of the present invention is a method as described herein, further comprising a step of receiving, after step e), an indication from the radiologist 1 of an interest in analysing the most urgent imaging study or a non-interest in analysing the most urgent imaging study. Where several radiologist appear to have the right criteria, the same study may appear on multiple worklists; in such case, the first radiologist to indicate his commitment in analysing the study is chosen.

According to one aspect of the invention studies from a particular client can be refused by a radiologist. This can be based on a poor feedback profile of the client and/or other factors. Optionally, the method may allow radiologists to refuse particular clients permanently. Refusal of a particular client or radiologist can be indicated by their characteristics.

To generate a report 21', the radiologist 1 may create an electronic file (e.g. Word, text, pdf) at his remote site. The file may contain text and optionally graphics. It can be prepared by typing or generated by dictation software. Radiologist 1 may be responsible for the quality and final editing of the report. The report 21' is then received 22 electronically by the method/system, having been sent by the radiologist 1. It can be sent by email, ftp upload, upload via a web page, or any known method of transferring electronic files.

The report 21" is subsequently made available 31 to the client 3. The report can be sent to the client for example by email, or made available for viewing at an internet address, or made available by any other means. Optional password or encryption protection may ensure confidentiality of the report. The version of the report received by the client 21''' may be identical to that 21' sent by the radiologist 1. Alternatively, the report 21''' may be watermarked, reformatted and/or edited by the method. The report 21''' may further be a linguistic translation of the original 21'.

Having received the report, the client 3 should be responsible for correct payment of the radiologist(s).

The client may receive a monthly overview of the work performed by one or more radiologists and the corresponding fees.

For every report 21''' received, the client 3 has the possibility to generate feedback 29 with regard to the quality of the radiologist's 1 work. This is preferably implemented using a web page. Features such as content and timeliness of the report may be used as the basis of the feedback. Feedback can take any form, such as, for example '+'/'0'/'−', meaning positive, neutral or negative respectively. Other forms of feedback include stars, percentages and/or actual written comments. Optionally, feedback may include the possibility to indicate refusal to work together with a particular radiologist in the future. In such a case, studies sent by this client will not appear on this radiologist's future worklist.

In addition, for every study 10 analysed and reported, the radiologist 1 may also have the possibility to generate feedback 28 with regard to the collaboration with the client 3. Features such as image and data quality, timeliness of payment may be used as the basis of the feedback. As above, feedback can take any form, such as, for example '+'/'0', '−', meaning positive, neutral or negative respectively. Other forms of feedback include stars, percentages and/or actual written comments. Optionally, feedback may include the possibility to indicate refusal to work together with a particular client in the future. In such a case, studies sent by this client will not appear on this radiologist's future worklist.

The feedback received can be collected to generate a rating 26 in respect of each radiologist 1 and client 3. A critical threshold for the rating 26 can be defined. Radiologists with a rating below the critical threshold can be de-registered i.e. removed from the community, either temporarily or permanently, according to predefined criteria known and accepted by the community members. The rating can be indicated in the respective characteristics of the client or radiologist.

The rating may be made available to all who are registered i.e. to both clients 3 and radiologists 1. This will allow both parties to decide whether to proceed with a transaction. Based on the rating, clients 3 may choose to refuse further collaboration with particular radiologist 1. If they indicate such a refusal, studies submitted by the client would not appear in the radiologist's worklist 11. Similarly, a radiologist 1 may choose to refuse to work with a particular client 3, in which case studies submitted by the client 3 would not appear in the radiologist's worklist 11.

Another embodiment of the invention is a computer program held on a computer readable medium for assisting in the analysis of clients' radiographic images by remote radiologists, which computer program is capable of performing the steps of the method described above.

Another embodiment of the invention is a system for assisting in the analysis of clients' radiographic image study by remote radiologists, which system is capable of performing the steps of the method.

With reference to FIG. 3, the said system comprises a processing means 39 whereby,
a) said means 39 is configured to make available over the Internet 34 a web page for the entry on a remote computer 38 of registration details of one or more radiologists, including an indication of their characteristics,
b) said means 39 is configured to make available over the Internet 34 a web page for the entry viewing on a remote computer 37 of registration details of one or more clients, including an indication of their characteristics,
c) said means 39 is configured to receive electronically an imaging study and associated data sent by a registered client from a remote computer 37,
d) said means 39 is configured to select a registered radiologist to analyse an imaging study by matching the radiologists' characteristics with the characteristics of the client and associated data of the imaging study of c),
e) said means 39 is configured to available over the Internet 34 to the registered radiologist or send electronically thereto, a list of imaging studies sent by clients,
f) said means 39 is configured to receive electronically a report of said analysed imaging study prepared by a registered radiologist of step d),
g) said means 39 is configured to make available over the Internet 34 to registered client of step c) or send electronically thereto, the report of step f),
h) said means 39 is configured to make available over the Internet 34 a web page for receiving a feedback score from the registered client regarding the quality of the registered radiologist's report,
i) said means 39 is configured to make available over the Internet 34 a web page for receiving a feedback score from the registered radiologist regarding collaboration with the client,
j) said means 39 is configured to calculate a rating profile of the registered radiologist and client based on received feedback scores.

Figure 5:
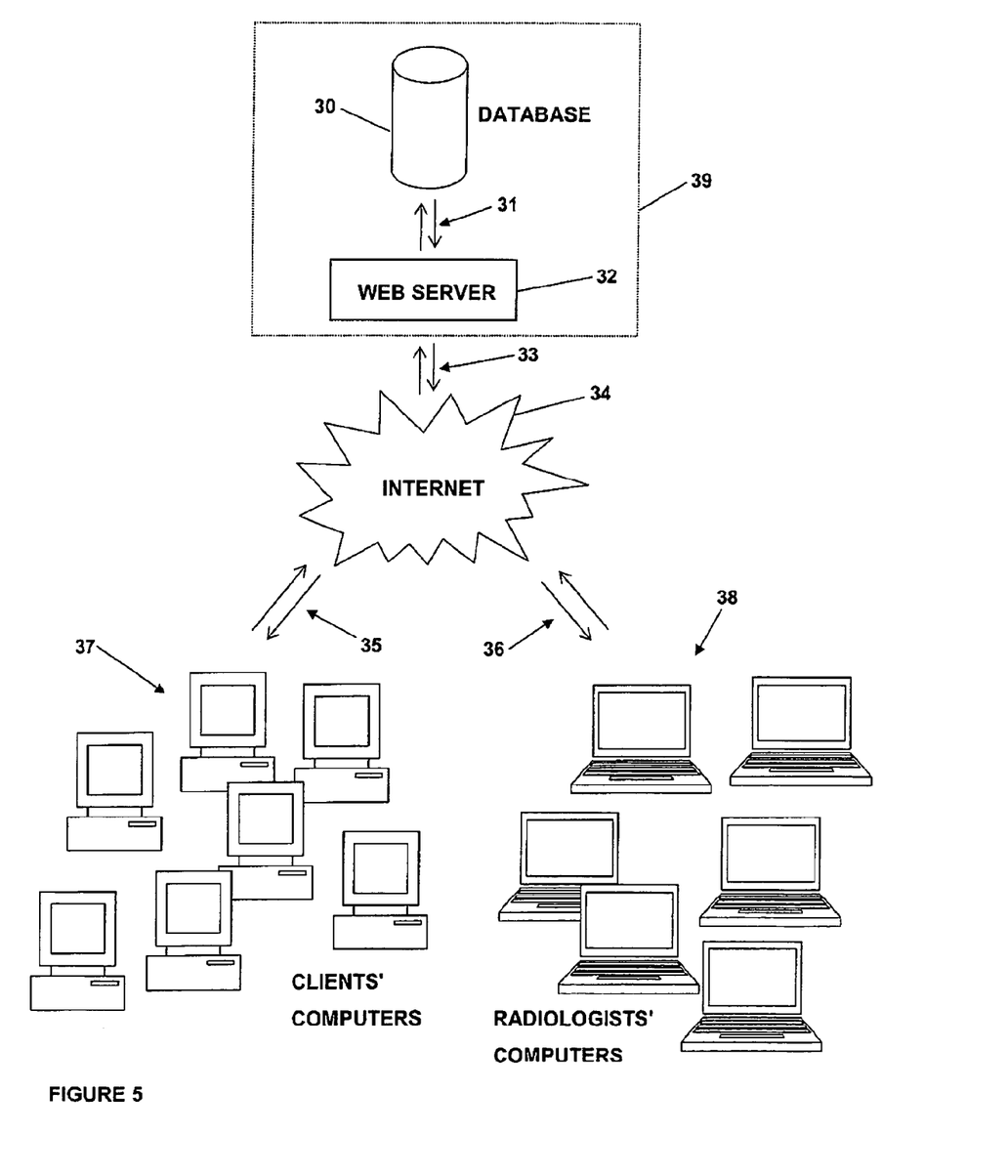
FIG. 5. Overview of a system of the invention

The processing means 39 can be performed, for example, by a suitably configured web server 32. Data regarding the radiologist and client registration details, characteristics, imaging studies, and/or reports may be held on a database 30. Such data would be transferred between said database 30 and the web server 32. Suitable configurations of the system can be readily determined by the person skilled in the art using presently available hardware and software and technologies.

The matching algorithm used by the invention compares a set of characteristics 7 of clients 3 and data associated with the imaging study 10 with a set of characteristics 4 of radiologists 1.

For example, the client may have the following characteristics (Char.) i.e. parameters which do not vary from study to study:
Char. 1: he wishes to work only with Benelux radiologists,
Char. 2: he is located in the Netherlands, Char. 3: he will not pay more than 100 EURS for any single report.

The client may provide the following data (Dat.) associated with a particular imaging study i.e. parameters which can vary from study to study:

Dat. 1: the study is a CT study.
Dat. 2: the patient is 6 years old.
Dat. 3: it is a study of the abdomen.
Dat. 4: he will pay no more than 30 FURS for this report.

The matching algorithm compares these characteristics and data with the characteristics of all registered radiologists. Those registered radiologists having indicated to have identical or matching characteristics will be selected. In this case, this would mean that a selected radiologist has indicated his interest and competence to read CT studies of the abdomen (Dat. 1 and 3), that he has indicated willingness and competence to report studies of pediatric patients (Dat 2), that he has indicated to fulfil all legal and other requirements needed to work as a radiologist for clients living in the Netherlands (Char. 1 and 2), and that his requested fee for that type of exam is 30 EUR or less (Dat. 4).

The method, system and computer program of the present invention provide a high degree of flexibility by bringing together the requirements of clients i.e. persons or organisations requiring the analysis of radiographic images with those of radiologists i.e. persons or organisations qualified to undertake analyses of radiographic images. Unlike practices in the art where a hospital or teleradiology group chooses the radiologists participating in the teleradiology service, the present invention welcomes all parties who are willing to participate, while ensuring high standards.

Furthermore, the selection of radiologists in the present invention is not biased according to any personal or subjective criteria. Matching is performed objectively. This is not the case in teleradiology hub, where selected cases are sent to radiologists with specific expertise, which radiologists can be known personally to the group. By having a choice of specialised radiologists available in the present invention, each having the same initial eligibility for selection, a much broader range of opinions can be gathered, which leads to an improved level of healthcare. Furthermore, the present invention permits a party to be a client and a radiologist at the same time.

The invention permits a system of quality control, where feedback ratings are available to all members. Every radiologist and every client can be rated, and individual parties blocked or welcomed. This is different from current practice where quality control is effected through, for example, systematic double reading of studies by a second radiologist, or supervision of a number of reports of a less experienced radiologist by a more experienced colleague, adherence to specific detailed standards regarding equipment for image viewing. Negative feedback in current practice is handled by the organisation, necessitating a code of practice and other levels of administrative burden.

An unlimited number of clients and radiologists can be registered with the invention. While, in traditional systems, clients have the choice between a limited number of service providers, the invention overcomes this limitation. As such, problems caused by regional imbalances between need for and availability of radiologists can be overcome at a global scale. Moreover, radiologists can build a clientele based on their true competence. Also, a mechanism is created for dynamic price setting: clients can indicate maximum prices or refuse radiologists requesting a too high fee. Radiologists can change their desired fee/exam to generate more or less work.

What is claimed is:

1. A method, implemented using one or more computers, for assisting in the analysis of a client's radiographic imaging study by a remote radiologist, the one or more computers configured to perform the following steps:
   a) receiving registration details for registration of one or more radiologists, the radiologist details including an indication of their characteristics, which includes an indication of the area of expertise of the radiologist, and an indication of the desired fee for carrying out an analysis of a particular image study,
   b) receiving registration details for registration of one or more clients, the client details including an indication that the one or more clients require analysis of a radiological imaging study, and an indication of the one or more clients' characteristics, which includes a maximum fee and/or fee range,
   c) receiving an imaging study and associated data which includes an indication of the body part imaged, sent by a registered client of step b),
   d) selecting, by at least one computer, one or more registered radiologists to analyze the imaging study by matching the radiologists' characteristics with the characteristics of the client and associated data of the imaging study of step c),
   e) making available to said selected registered radiologists, a worklist of the at least one or more imaging studies sent by clients including the imaging study of step c),
   f) receiving a report of said analyzed imaging study prepared by a registered radiologist of step e),
   g) making available the report of step f) to the registered client of step c),
   h) receiving a feedback score from the registered client regarding the quality of the registered radiologist's report,
   i) receiving a feedback score from the registered radiologist regarding collaboration with the client,
   j) calculating a rating profile including ratings of the registered radiologist and client based on received feedback scores of steps h) and i), and
   k) making available, by the at least one computer, in the respective characteristics of the client and radiologist, the calculated ratings from the rating profile of step j) to all registered clients and radiologists.

2. The method according to claim 1, wherein the worklist of step e) is ranked according to urgency.

3. The method according to claim 2, wherein the most urgent imaging study is removed from the worklist of step e) after receiving an indication that one of the selected radiologists has opened said imaging study.

4. The method according to claim 2, wherein the most urgent imaging study is removed from the worklist of step e) after the report of step f) has been received.

5. The method according to claim 2, further comprising a step after step e) of:
   receiving an indication from a selected radiologist of an interest in analyzing the most urgent imaging study or a non-interest in analyzing the most urgent imaging study.

6. The method according to claim 3, wherein the most urgent imaging study is removed from the worklist of step e) after receiving said indication.

7. The method according to claim 1 comprising the step of making available the rating profile of said radiologist and client to all registered radiologists and clients.

8. The method according to claim 1, wherein the characteristics of the client further comprise one or more of:
   preferred geographical location of the radiologist, and
   any other characteristic.

9. The method according to claim 1, wherein the characteristics of the radiologists further comprise one or more of:
- indication of which countries, regions, countries, localities and/or hospitals he wishes to work,
- indication of the type(s) of imaging study or studies he wants to analyze,
- indication of whether he wants to act as a primary reader, as secondary reader, or both, indication of the desired fee for carrying out an analysis of a particular image
- the wish to display a curriculum vitae,
- indication of availability,
- indication of availability for stat readings,
- an indication of willingness to work together with one or more other registered radiologists to form a reading group, and
- any other characteristic.

10. The method according to claim 9, wherein a reading group of one or more other registered radiologists willing to work together is permitted when the characteristics of the radiologists include an indication of availability for stat readings.

11. The method according to claim 1, where the type of imaging study is selected according to one or more of the following criteria:
- type of imaging instrument,
- body part, and
- patient characteristic.

12. The method according to claim 2, wherein the ranking is determined by
- the time of arrival of images at the central database and/or
- a requested turnaround time by the client.

13. The method according to claim 1, wherein the worklist of step e) is filtered to exclude clients refused by said radiologist.

14. The method according to claim 1, wherein the worklist of step e) is filtered to exclude clients which have refused said radiologist.

15. The method according to claim 1 where a radiologist receives an alert when his worklist has been updated.

16. The method according to claim 15, when said alert is by telephone, SMS messaging or email.

17. A non-transitory computer readable medium comprising a computer program for assisting in the analysis of clients' radiographic image study by remote radiologists, wherein the computer program is configured to:
a) receive registration details for registration of one or more radiologists, the radiologist details including an indication of their characteristics, which includes an indication of the area of expertise of the radiologist, and an indication of the desired fee for carrying out an analysis of a particular image study,
b) receive registration details for registration of one or more clients, the client detail including an indication that the one or more clients require analysis of a radiological imaging study, and an indication of the one or more clients' characteristics, which includes a maximum fee and/or fee range,
c) receive an imaging study and associated data sent by a registered client of step b),
d) select one or more registered radiologists to analyze the imaging study by matching the radiologists' characteristics with the characteristics of the client and associated data of the imaging study of step c),
e) make available to said selected registered radiologists, a worklist of the at least one or more imaging studies sent by clients including the imaging study of step c),
f) receive a report of said analyzed imaging study prepared by a registered radiologist of step e),
g) make available the report of step f) to the registered client of step c),
h) receive a feedback score from the registered client regarding the quality of the registered radiologist's report,
i) receive a feedback score from the registered radiologist regarding collaboration with the client, and
j) calculate a rating profile including ratings of the registered radiologist and client based on received feedback scores of h) and i), and
k) make available, in the respective characteristics of the client and radiologist, the calculated ratings from the rating profile of step j) to all registered clients and radiologists.

18. A computer system for assisting in the analysis of clients' radiographic image study by remote radiologists, the computer system comprising a processor configured to:
a) receive registration details for registration of one or more radiologists, the radiologist details including an indication of their characteristics, which includes an indication of the area of expertise of the radiologist, and an indication of the desired fee for carrying out an analysis of a particular image study,
b) receive registration details for registration of one or more clients, the client details including an indication that the one or more clients require analysis of a radiological imaging study, and an indication of the one or more clients' characteristics, which includes a maximum fee and/or fee range,
c) receive an imaging study and associated data sent by a registered client of step b),
d) select one or more registered radiologists to analyze the imaging study by matching the radiologists' characteristics with the characteristics of the client and associated data of the imaging study of step c),
e) make available to said selected registered radiologists, a worklist of the at least one or more imaging studies sent by clients including the imaging study of step c),
f) receive a report of said analyzed imaging study prepared by a registered radiologist of step e),
g) make available the report of step f) to the registered client of step c),
h) receive a feedback score from the registered client regarding the quality of the registered radiologist's report,
i) receive a feedback score from the registered radiologist regarding collaboration with the client, and
j) calculate a rating profile including ratings of the registered radiologist and client based on received feedback scores of h) and i), and
k) make available, in the respective characteristics of the client and radiologist, the calculated ratings from the rating profile of step j) to all registered clients and radiologists.

19. The computer system according to claim 18, whereby,
a) said processor is configured to make available over the Internet a web page for the entry on a remote computer of registration details of one or more radiologists, including an indication of their characteristics,
b) said processor is configured to make available over the Internet a web page for the entry viewing on a remote computer of registration details of one or more clients, including an indication of their characteristics, c) said processor is configured to receive electronically an imaging study and associated data sent by a registered client from the remote computer of step b), d) said processor is configured to select a registered radiologist to analyze an imaging study by matching the radiologists' characteristics with the characteristics of the client and associated data of the imaging study of c), e) said processor is configured to make available over the Internet to the registered radiologist or to send electronically thereto, a worklist of imaging studies sent by clients, f) said processor is configured to receive electronically a report of said analyzed imaging study prepared by the registered radiologist of step d), g) said processor is configured to make available over the Internet to the registered client of step c) or to send electronically thereto, the report of step f), h) said processor is configured to make available over the Internet a web page for receiving a feedback score from the registered client regarding the quality of the registered radiologist's report, i) said processor is configured to make available over the Internet a web page for receiving a feedback score from the registered radiologist regarding collaboration with the client, j) said processor is configured to calculate a rating profile of the registered radiologist and client based on received feedback scores of h) and i), and k) said processor is configured to make available over the Internet, in the respective characteristics of the client and radiologist, the calculated ratings from the rating profile of step j) to all registered clients and radiologists.

\* \* \* \* \*

UNITED STATES PATENT AND TRADEMARK OFFICE
CERTIFICATE OF CORRECTION

| | |
|---|---|
| PATENT NO. | : 8,468,032 B2 |
| APPLICATION NO. | : 12/373031 |
| DATED | : June 18, 2013 |
| INVENTOR(S) | : Van Hoe |

It is certified that error appears in the above-identified patent and that said Letters Patent is hereby corrected as shown below:

In the Drawings:

Sheet 1 of 5 (Reference Numeral 4, FIG. 1) at line 2, Change "CHARACTERISICS" to --CHARACTERISTICS--.

Sheet 1 of 5 (Reference Numeral 7, FIG. 1) at line 2, Change "CHARACTERISICS" to --CHARACTERISTICS--.

Sheet 2 of 5 (Reference Numeral 4, FIG. 2) at line 2, Change "CHARACTERISICS" to --CHARACTERISTICS--.

Sheet 2 of 5 (Reference Numeral 7, FIG. 2) at line 2, Change "CHARACTERISICS" to --CHARACTERISTICS--.

Sheet 3 of 5 (Reference Numeral 4, FIG. 3) at line 2, Change "CHARACTERISICS" to --CHARACTERISTICS--.

Sheet 3 of 5 (Reference Numeral 7, FIG. 3) at line 2, Change "CHARACTERISICS" to --CHARACTERISTICS--.

Sheet 4 of 5 (Reference Numeral 4, FIG. 4) at line 2, Change "CHARACTERISICS" to --CHARACTERISTICS--.

Sheet 4 of 5 (Reference Numeral 7, FIG. 4) at line 2, Change "CHARACTERISICS" to --CHARACTERISTICS--.

In the Specification:

In column 4 at line 36 (approx.), Change "invention" to --invention.--.

In column 7 at line 17, Change "indicated" to --indicated.--.

In column 11 at line 9, Change "FURS" to --EURS--.

Signed and Sealed this
First Day of April, 2014

Michelle K. Lee
*Deputy Director of the United States Patent and Trademark Office*